United States Patent
Sarstedt

(10) Patent No.: US 7,294,111 B2
(45) Date of Patent: Nov. 13, 2007

(54) BLOOD-DRAWING DEVICE

(75) Inventor: Walter Sarstedt, Nümbrecht (DE)

(73) Assignee: Sarstedt AG & Co., Numbrecht (DE)

( * ) Notice: Subject to any disclaimer, the term of this patent is extended or adjusted under 35 U.S.C. 154(b) by 0 days.

(21) Appl. No.: 10/499,748

(22) PCT Filed: Dec. 16, 2002

(86) PCT No.: PCT/DE02/04588

§ 371 (c)(1),
(2), (4) Date: Aug. 12, 2004

(87) PCT Pub. No.: WO03/055390

PCT Pub. Date: Jul. 10, 2003

(65) Prior Publication Data
US 2005/0043650 A1  Feb. 24, 2005

(30) Foreign Application Priority Data
Dec. 21, 2001  (DE) ................. 101 63 716

(51) Int. Cl.
*A61B 5/00*  (2006.01)
(52) U.S. Cl. ..................................... 600/577
(58) Field of Classification Search ............... 600/577, 600/576; 604/162, 156, 411, 110, 192
See application file for complete search history.

(56) References Cited
U.S. PATENT DOCUMENTS 4,378,812 A    4/1983  Sarstedt
4,449,539 A    5/1984  Sarstedt
4,772,265 A *  9/1988  Walter ................. 604/164.08
5,154,285 A   10/1992  Hollister
5,277,311 A    1/1994  Hollister
5,360,012 A * 11/1994  Ebara et al. .............. 600/577
5,755,701 A    5/1998  Sarstedt
2004/0210196 A1* 10/2004 Bush, Jr. et al. ............ 604/192

FOREIGN PATENT DOCUMENTS

DE  29 03 167    7/1980
DE  30 49 503    7/1982
DE  692 25 60   12/1994

* cited by examiner

Primary Examiner—Max F. Hindenburg
Assistant Examiner—Fangemonique Smith
(74) Attorney, Agent, or Firm—Andrew Wilford

(57) ABSTRACT

A blood-drawing device has a specimen tube having a projecting tip having an outer connection region of a predetermined diameter and a guide sleeve fittable over the tip and having an inner resilient part. The inner resilient part has an inside diameter smaller than the diameter of the connection region. A needle fitted to the guide sleeve is surrounded by an elastomeric tubular needle shield inward from the guide sleeve. The sleeve can move between an outer position with the needle shield extending inward past the inner needle end and the resilient part offset outward from the connection region and an inner position with the needle end in the specimen tube, the needle shield compressed between the sleeve and the specimen tube, and the resilient part fitting tightly around the connection region and deformed outwardly thereby such that the resilient part grips the connection region.

9 Claims, 3 Drawing Sheets

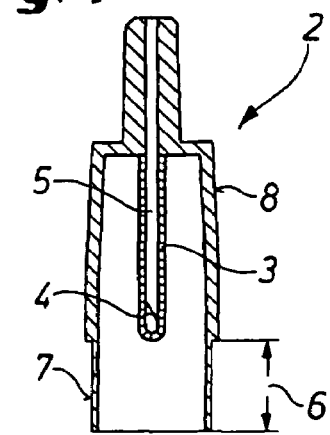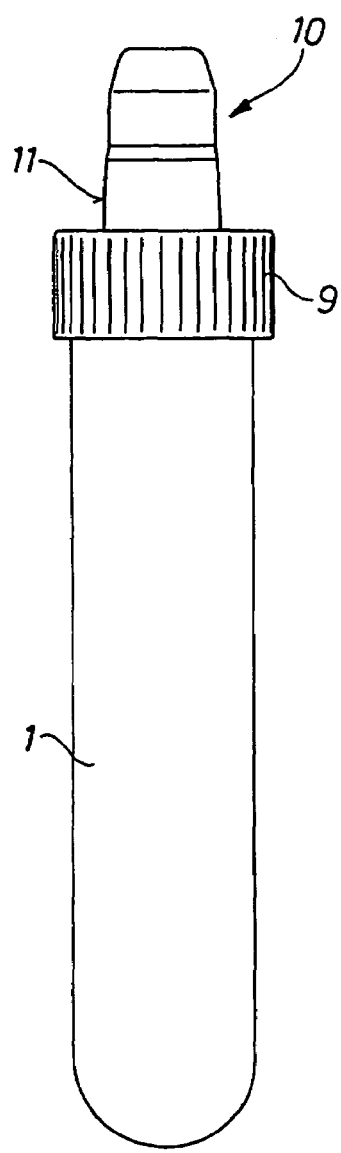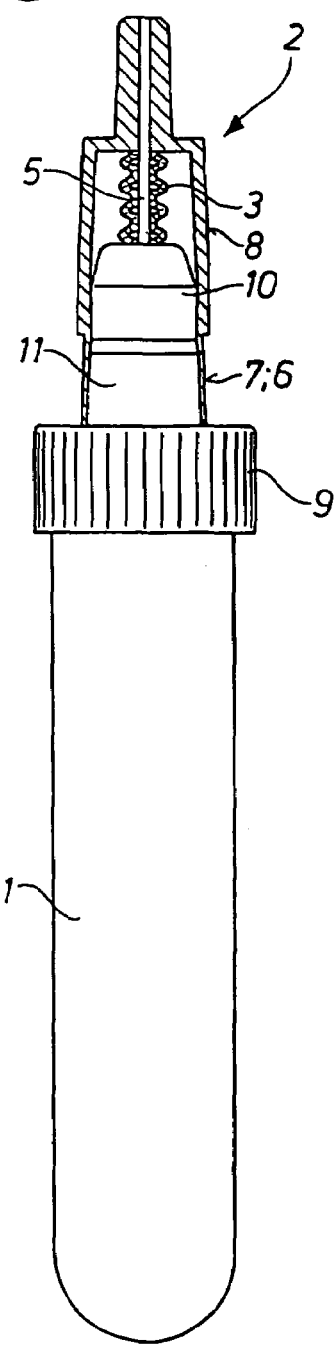

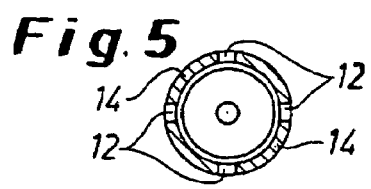
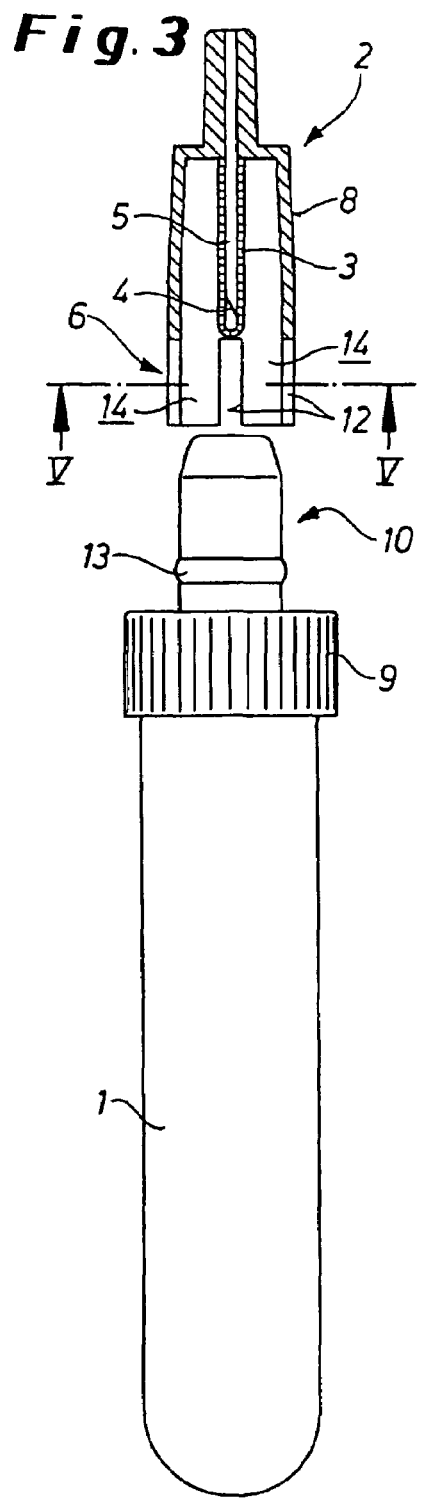
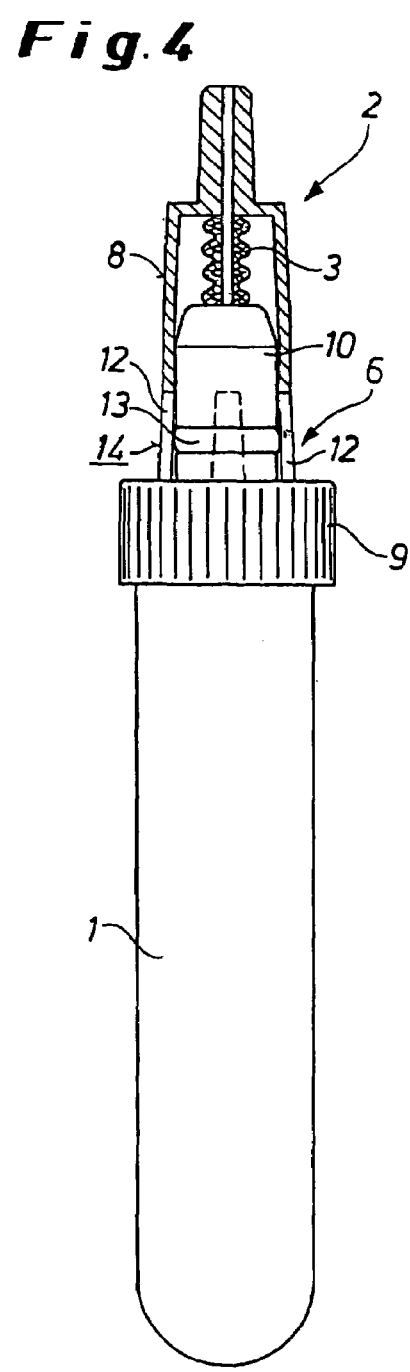

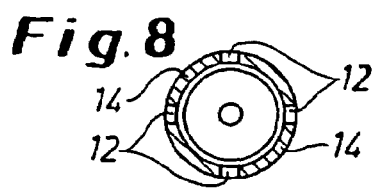
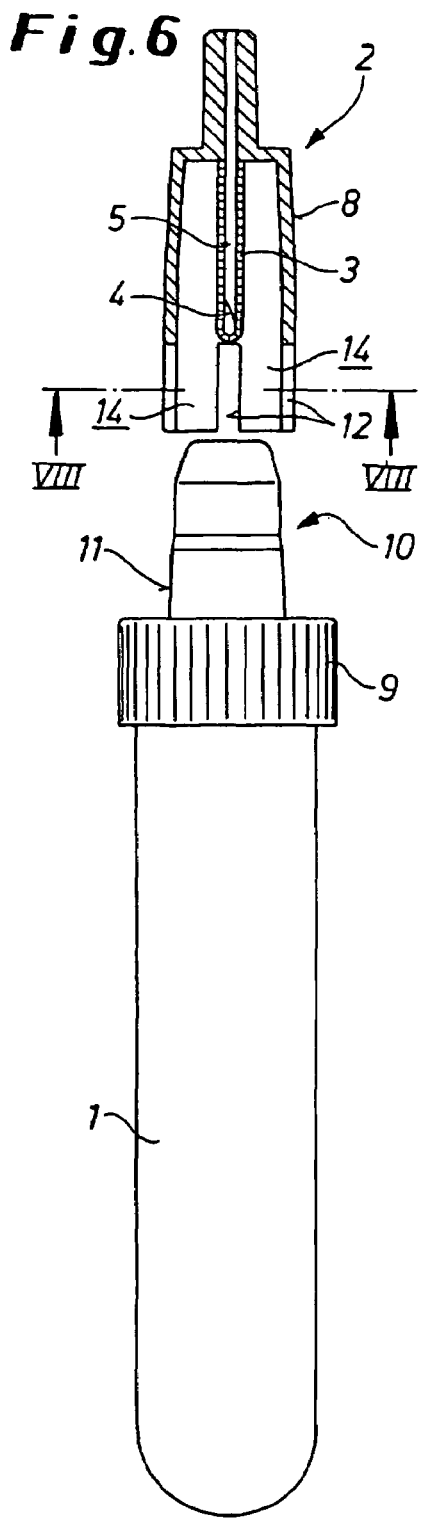
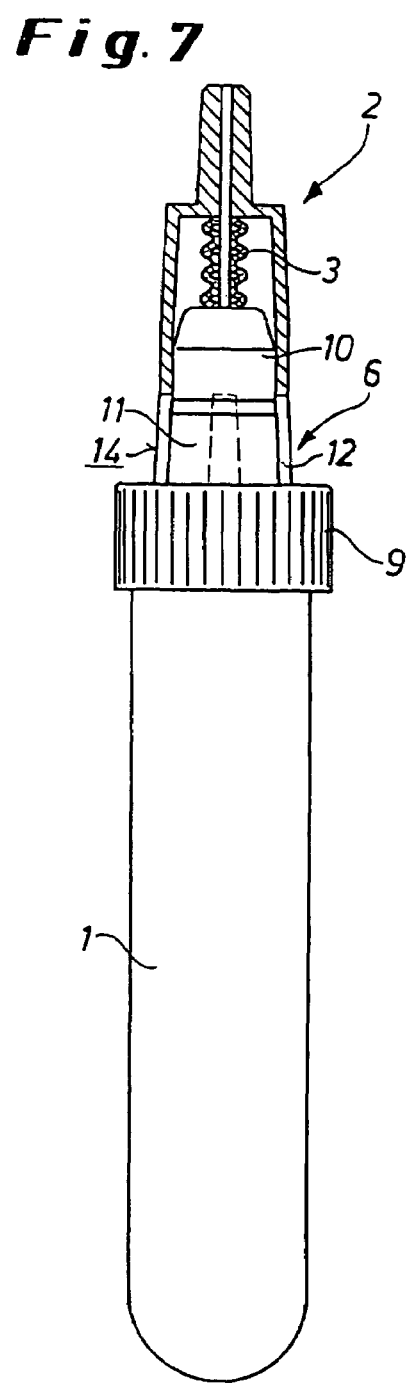

BLOOD-DRAWING DEVICE

CROSS REFERENCE TO RELATED APPLICATIONS

This application is the US national phase of PCT application PCT/DE02/04588, filed 16 Dec. 2002, published 10 Jul. 2003 as WO 03/055390, and claiming the priority of German patent application 10163716.0 itself filed 21 Dec. 2001.

FIELD OF THE INVENTION

The invention relates to a device for drawing body fluids, having a specimen tube having at an outer end a tip with a pierceable plug for a guide sleeve fittable on the tip and provided on its side turned toward the tip with a needle and with an elastomeric needle-shield tube and on the side turned away from the tip with a connection fitting or the opposite end of a double needle.

BACKGROUND OF THE INVENTION

Such devices are for example used for drawing blood from a bottle or bag or to take a specimen from a collection vessel of for example urine. In every case there is the problem that the elastomeric needle-shield tube that surrounds the needle and that is collapsed like a bellows when the guide sleeve is fitted to or installed on the tip exerts a substantial spring return force acting against the forces that retain the guide sleeve on the tip, with the result that the guide sleeve is pushed off the tip. In order to get around this problem, various measures are taken.

In the blood-drawing device described in German 3,049, 503 (US equivalent U.S. Pat. No. 4,449,539), the cap closing the outer end of the specimen tube has a cylindrical axially extending tip. The tip is closed at its outer end by a pierceable plug that is trapped between an inner centrally apertured wall of the tip and an outer-end rim. The tubular guide sleeve, which has on its outer end a holder for a double-ended and pointed needle whose outer end is intended for insertion into a vein while its inner end projects so far into the guide sleeve that when the guide sleeve is fitted to the specimen tube it pokes through the plug, is axially shiftable and rotatable on the tip. The inner end of the needle projecting from the guide tube is contained in a bag-like tube (elastomeric needle-shield tube) of such length that the inner point of the needle does not initially reach to its closed end.

In order that the guide sleeve stays on the tip in spite of the spring pressure from the elastomeric needle-shield tube, the tip is provided with a laterally projecting bump for holding the double-ended needle that fits in an L-shaped slot in the guide sleeve. This holding bump projecting through the slot in the periphery forms a sort of bayonet latch that secures the guide sleeve to the double needle. Such a latch-ensures a solid connection of the fitted-together parts of the blood-drawing device, but increase its production cost. In addition the coupling and decoupling or latching of the guide sleeves requires that the holding bump first be aligned by turning of the specimen tube with the closing screw or plug cap to align with the slot, which requires some adept manipulation so that the parts can be properly aligned.

German 692 25 609 (US equivalent U.S. Pat. Nos. 5,154, 285 and 5,277,311) describes a protective housing for a needle screwed into a needle holder. Here the protective housing is rotatable on the holder to which end the protective housing has a ring forming an inwardly open groove in which a ridge on a tip of the holder fits.

OBJECT OF THE INVENTION

It is an object of the invention to provide a device of the above-described type with a simple and reliable connection for the two interfitting parts that can be produced at low cost, is easy to use, and provides a solid enough retention to resist the spring force (return force) of the needle-shield tube tending to open it.

SUMMARY OF THE INVENTION

This object is achieved in that the guide sleeve is made of a relatively stiff material and has on its outer end adjacent a grip region a resilient part, the tip having a connection region of larger diameter than an inside diameter of the guide sleeve, the larger-diameter region of the tip spreading the resilient part such that it solidly grips the tip in a use position.

The diameter relationships of regions of the tip and guide sleeve with one of them oversized to produce the interfit of the resilient part of the guide sleeve and the tip to produce the desired holding force are created by increasing the size of the tip in the seat region, for example by a ridge, cylinder, ribs, taper, segments, or the like. The system of this invention achieves several advantages. As a result of the limited length of the resilient part relative to the overall length of the guide sleeve, there is sufficient gripping force in the defined regions of the end portions for the necessary hold, while a relatively long portion of the guide sleeve remains as usual rigid and not resilient, so that during installation on and removal from the specimen tube one can use a grip region having nothing to do with the gripping action. The spreading effected by the short enlarged diameter of the tip is effective solely in a short region offset from the grip surface. This spreading of the guide sleeve makes it possible to precisely establish and set the amount of hold so that the grip is sufficient to overcome the pushing force of the compressed elastomeric needle shield, thereby preventing the guide sleeve from being pushed off the tip. In spite of the relatively small diameters of the mating parts (guide sleeve and tip) sufficient holding force is obtained so that the parts can be more easily and simply pushed together and pulled apart than a standard tapered luer connection. Complex manipulation is not needed since the parts do not need a precise alignment.

In order to set the resilience of the guide sleeve in the region offset from the rigid grip region, the inner end of the sleeve can be of the same thickness as the rest of the sleeve but be formed with longitudinal slits having a length equal to the length of the resilient region. The slit or slits allow the otherwise rigid material to flex sufficiently for easy use and to still provide the necessary holding force (solid hold) against the spring force of the needle-shield tube.

Alternatively instead of slits the resilient region can be made less thick or of such a material that it produces the desired holding force. When the tip is formed with an annular ridge or a tapered region of a diameter exceeding the inner diameter of the guide sleeve it is possible to injection mold the tip or a cap forming the tip without having to use a mold with movable parts. Even with for example uniformly angularly spaced bumps around the tip or even one such bump the guide-sleeve portion will hold well enough when installed that the guide sleeve is solidly connected with the tip and thus provides the exact prestress or holding force needed.

BRIEF DESCRIPTION OF THE DRAWING

Further embodiments and particular features of the invention are seen in the claims and the following description of embodiments of a blood-drawing device according to the invention as shown in the drawing. Therein:

FIG. 1 is a partly sectional and exploded view of a specimen tube with a guide sleeve;

FIG. 2 is a side view partly in axial section through the guide tube fitted over the tip of the specimen tube of FIG. 1;

FIG. 3 is a partly sectional and exploded view of another embodiment of the specimen tube and guide sleeve;

FIG. 4 is a view like FIG. 2 of the guide tube fitted over the tip of the specimen tube of FIG. 3;

FIG. 5 is a cross section taken along line V-V of FIG. 3;

FIG. 6 is a partly sectional and exploded view of yet another specimen tube and guide sleeve;

FIG. 7 is a view like FIG. 2 of the guide tube fitted over the tip of the specimen tube of FIG. 6; and FIG. 8 is a cross section taken along line VIII-VIII of FIG. 6.

SPECIFIC DESCRIPTION

A blood-drawing device according to FIGS. 1 and 2 comprises a specimen tube 1 with a tip 10 and guide sleeve 2 provided in all embodiments for example with a luer fitting and holding a needle 5 having a point 4 and surrounded by an elastomeric shield tube 3. In other embodiments of the guide sleeve, its side turned away from the tip has a connector or the outer part of a double needle. The side of the guide sleeve 2 turned toward the specimen tube 1 is provided with a resilient part 6 formed in FIGS. 1 and 2 as a sleeve 7 of lesser wall thickness than the rest of the guide sleeve 2. Above this part 6 the guide sleeve 2 is formed of relatively stiff plastic with uniform thickness and a thus offers a grip surface 8 that is particularly convenient for installing and removing it from the specimen tube 1.

The specimen tube 1 is closed at its upper end by a cap 9. It has the tip 10 that starting about halfway along its length has a large-diameter frustoconical region 11 that is slightly bigger than an inside diameter of the guide sleeve 2. When the blood-drawing device is used the guide sleeve 2 is fitted to the tip 10 of the specimen tube 1 as shown in FIG. 2. When the guide sleeve 2 is fitted to the tip 10, the needle 5 pierces with its tip 4 through an unillustrated plug fitted in the cap 9 until the needle tip is exposed inside the specimen tube 1; the also pierced elastomeric needle-shield tube 3 is crushed like a bellows as shown in FIG. 2. The fit between the part 6 and the region 11 of the sleeve 2 on the tip 10 is enough to resist the spring return force of the axially elastically compacted needle-shield tube 3, since the oversize tip 10 is surrounded tightly by the coupling region with the necessary force.

The embodiments of the blood-drawing device according to FIGS. 3 to 5 or 6 to 8 only differ from FIGS. 1 and 2 by the construction of the resilient part of the guide sleeve or of the tip 10 of the cap 9 of the specimen tube 1 so that similar parts have the same reference numerals; what is common to all embodiments is that the oversize tip 10 spreads the elastic portion 7 of the guide sleeve 6 so that the guide sleeve 6 is solidly connected with the tip 10.

In the blood-drawing device according to FIGS. 3 to 5 the elasticity of the part 6 near the grip region 8 is provided here by four longitudinal slits 12 (see FIG. 5) in the same region that define or delimit deflectable fingers 14. The tip 10 here has a raised portion constituted as a diameter-increasing ring or ridge 13 that spreads the section 6 or the fingers 14 defined by the slits 12 when the guide sleeve 2 is fitted to the tip 10 (see FIG. 4) so that the guide sleeve 2 is solidly secured to the specimen tube 1 with a force that is greater than the oppositely effective return force of the elastomeric needle-shield tube 3.

The variant on the blood-drawing device according to FIGS. 6 to 8 also has a guide sleeve 2 with longitudinal slits 12 and fingers 14 defined thereby in the part 6 as described above with reference to FIGS. 3 to 5. To spread the part 6 when fitting the guide sleeve 2 to the tip 10 of the cap 9 of the specimen tube 1, the tip 10 is provided with a frustoconical region 11 at the base of the tip as shown in FIGS. 1 and 2.

Regardless of the actual construction for the fitting of the part 6 of the guide sleeve 2 onto the tip 10 of the cap 9, in every embodiment the larger outside diameter of the tip portion 11 fitting inside the part 7 of the guide sleeve 6 produces a clamping action providing a very good hold. This is also true when instead of a raised surface as with a complementary taper or an outer ridge, only point-like bumps are provided. It is also worth mentioning that the flexibility of the part 6 compensates out manufacturing tolerances, making production easier.

The invention claimed is:

1. A blood-drawing device comprising:
a specimen tube having a projecting tip having an outer side surface forming a connection region of a predetermined diameter;
a guide sleeve fittable over the tip and unitarily formed with a generally cylindrical thick and generally rigid outer grip part of predetermined diameter and a thin inner resilient, generally cylindrical, and radially deformable part, the inner resilient part having an inside diameter smaller than the predetermined diameter of the connection region and generally the same as the predetermined diameter of the outer grip part, the inner part being an axial extension of the outer part;
a needle fitted to the guide sleeve and having an inner end; and
an elastomeric tubular needle shield surrounding the needle inward from the guide sleeve, the sleeve being movable between
an outer position with the inner needle end out of the specimen tube, the needle shield extending inward past the inner needle end, and the resilient part offset outward from the connection region and
an inner position with the inner needle end traversing the shield and projecting inward into the specimen tube, the needle shield compressed between the sleeve and the specimen tube, and the resilient part fitting tightly around the connection region and deformed outwardly thereby such that the resilient part grips the connection region.

2. The blood-drawing device defined in claim 1 wherein the specimen tube, sleeve, needle, and needle shield are all generally coaxial.

3. The blood-drawing device defined in claim 2 wherein the connection region is annular and radially outwardly directed.

4. The blood-drawing device defined in claim 3 wherein the inner resilient part is annularly continuous and elastically deformable.

5. The blood-drawing device defined in claim 3 wherein the inner resilient part is formed with a plurality of axially inwardly open slots subdividing the resilient part into a plurality of axially extending and radially elastically deformable fingers.

6. The blood-drawing device defined in claim 3 wherein the connection region is smooth and the resilient part has a complementary smooth inner surface.

7. The blood-drawing device defined in claim 3 wherein the connection region is frustoconical.

8. The blood-drawing device defined in claim 3 wherein the connection region is formed with an annular and radially outwardly projecting ridge.

9. The blood-drawing device defined in claim 3 wherein the outer grip part is tubular.

* * * * *